United States Patent
Bolz et al.

[11] Patent Number: 5,571,158
[45] Date of Patent: Nov. 5, 1996

[54] STIMULATION ELECTRODE

[75] Inventors: Armin Bolz; Max Schaldach, both of Erlangen, Germany

[73] Assignee: Biotronik Mess- und Therapiegeraete GmbH & Co. Ingenieurbuero Berlin, Berlin, Germany

[21] Appl. No.: 193,042

[22] PCT Filed: Aug. 6, 1992

[86] PCT No.: PCT/DE92/00658

§ 371 Date: Jun. 23, 1994

§ 102(e) Date: Jun. 23, 1994

[87] PCT Pub. No.: WO93/02739

PCT Pub. Date: Feb. 18, 1993

[30] Foreign Application Priority Data

Aug. 6, 1991 [DE] Germany ............. 41 26 362.6
Mar. 5, 1992 [DE] Germany ............. 42 07 368.5

[51] Int. Cl.⁶ ............................................. A61N 1/04
[52] U.S. Cl. ............................................. 607/121
[58] Field of Search ................... 607/119–129; 128/642

[56] References Cited

U.S. PATENT DOCUMENTS

| | | | |
|---|---|---|---|
| 4,011,861 | 3/1977 | Enger | 128/642 |
| 4,101,984 | 7/1978 | MacGregor | 607/121 |
| 4,407,302 | 10/1983 | Hirshorn et al. | 607/121 |
| 4,408,604 | 10/1983 | Hirshorn et al. | 607/121 |
| 4,506,680 | 3/1985 | Stokes | 607/120 |
| 4,776,338 | 10/1988 | Lekholm et al. | |
| 4,784,160 | 11/1988 | Szilagyi | |
| 5,181,526 | 1/1993 | Yamasaki | 607/121 |
| 5,215,088 | 6/1993 | Normann et al. | 128/642 |

FOREIGN PATENT DOCUMENTS

| | | |
|---|---|---|
| 0057877 | 2/1982 | European Pat. Off. |
| 085743 | 8/1982 | European Pat. Off. |
| 115778 | 1/1984 | European Pat. Off. |
| 0126981 | 4/1984 | European Pat. Off. |
| 116280 | 7/1987 | European Pat. Off. |
| 117972 | 8/1987 | European Pat. Off. |
| 3300672 | 7/1984 | Germany. |
| 3300668 | 7/1984 | Germany. |
| 3300694 | 8/1984 | Germany. |
| 3438221 | 4/1986 | Germany. |
| 2613052 | 7/1987 | Germany. |
| 4112936 | 10/1991 | Germany. |
| 6047095 | 2/1994 | Japan ............. 607/122 |
| 285126 | of 1971 | U.S.S.R. |
| 284244 | of 1971 | U.S.S.R. |

OTHER PUBLICATIONS

Biomedizinische Technik, vol. 34, No. 7/8, Aug. 1989, Berlin, Germany pp. 185–190, Schaldach "Titannitrid–Herzschrittmacher–Elektroden".

*Primary Examiner*—William E. Kamm
*Attorney, Agent, or Firm*—Spencer & Frank

[57] ABSTRACT

A stimulation electrode having a porous surface coating whose active surface area is significantly greater than the surface area defined by the geometric shape of the electrode, wherein the surface coating comprises an inert material, i.e. a material having no or only a very slight oxidation tendency, wherein the material of the surface coating is formed from an inert element, an inert chemical compound and/or an inert alloy, and the active surface area, by virtue of its fractal-like geometry, is greater by a factor of at least one thousand than the surface area defined by the basic geometric shape of the electrode.

8 Claims, 4 Drawing Sheets

STIMULATION ELECTRODE

CROSS-REFERENCE TO RELATED APPLICATION

This application is the U.S. national stage of PCT/DE92/00658 filed Aug. 6, 1992.

BACKGROUND OF THE INVENTION

1. Field of the Invention

The invention relates to a stimulation electrode having a porous surface coating whose active surface area is essentially larger than the surface area defined by the geometrical basic shape of the electrode.

2. Description of the Related Art

From an electrical standpoint, the phase limit between a solid body, that is, between the stimulation electrode of a pacemaker and an electrolyte, can be described in a simplified manner as a parallel switching of the phase limit capacity, i.e. the Helmholtz capacity $C_H$, and the Faraday resistance $R_F$, with which the line resistance $R_L$ is connected in series. The impedance of the electrode system $Z_{DL}$ is a function of the frequency $\omega$ of the applied voltage in accordance with the following equation:

$$Z_{DL} = R_L + \left( \frac{1}{R_F^2} + \omega^2 C_H^2 \right)^{-1/2} \quad (1)$$

A specified charge Q is required to stimulate the heart muscle, which charge can be calculated from the integral of the stimulation current I(t) over the pulse width T. Consequently, the impedance of the electrode system $Z_{DL}$ can likewise be minimized when the quantity of energy required for stimulating the heart is minimized:

$$E \approx \int_0^T U(t)I(t)dt$$

Because the line resistance $R_L$ is constant, the Faraday resistance $R_F$ is defined with the following equation $$R_F = \frac{R_o}{A} \quad (2)$$

where $R_o$ is a constant transfer resistance and A is the active surface area, and the Helmholtz capacity $C_H$ is defined as follows:

$$C_H = \epsilon \cdot \epsilon_o \frac{A}{d}, \quad (3)$$

where $\epsilon$ is the dielectric constant of the added water dipoles, $\epsilon_o$ is the dielectric constant of the vacuum and d is the thickness of the Helmholtz layer, the enlargement of the active surface area of the electrode according to (3) leads to an increase in the Helmholtz capacity $C_H$ and, according to (2), to a reduction in the Faraday resistance $R_F$. According to (1), both then have as a consequence a reduction in the impedance $Z_{DL}$ and in the required quantity of energy E. The active surface area A can be changed particularly by the enlargement in the electrode and/or by structuring of the electrode surface area.

Stimulation electrodes whose electrochemically active surfaces are enlarged by means of a porous layer composed of a carbide, nitride or carbon nitride, at least one of the metals including titanium, vanadium, zirconium, niobium, molybdenum, hafnium, tantalum or tungsten are already known from EP-A-0,117,972, EP-A-0,116,280 and EP-A-0,115,778.

A drawback of these known porous electrode coatings is that the overall capacity of the implanted electrodes decreases slowly over time, resulting in a corresponding increase in the required quantity of energy. Hence, the stimulation voltage must be selected relatively high in order to exceed the threshold response of the patient with the pulse energy over the long term. However, to emit the increased energy, an increase in the voltage of the pulses, which again results in an enlargement of the energy sources—and thus an enlargement in the housing—in implanted systems. The increase in pulse energy is accompanied by an increase in the polarization voltage, so that, after completed stimulation, the conventionally employed counterpulses must be correspondingly increased to prevent the effects of the polarization voltage on the input amplifier of the pacemaker.

It is an object of the invention to improve a stimulation electrode of the above-mentioned type in such a way that, on the one hand, the energy required for stimulation can also remain low in the long term and, on the other hand, that a reliable recognition of effectiveness is assured with simple measures.

SUMMARY OF THE INVENTION

This object is attained by providing a stimulation electrode having a porous surface coating whose active surface area is essentially larger than the surface area defined by the geometrical basic shape of the electrode, characterized in that the surface coating is composed of an inert material, i.e. a material with no or a very slight oxidation tendency, wherein the material of the surface coating is formed from an inert element, an inert chemical compound and/or an inert alloy, wherein, by virtue of the fractal-type spatial geometry, the active surface area is greater by a factor of at least one thousand times than the surface area defined by the geometric basic shape of the electrode.

The invention is based on the recognition that the materials of the known electrodes, and particularly titanium, vanadium, zirconium and niobium, exhibit a tendency toward partially extreme oxidation, and that, during contact with aqueous electrolytes, this strong oxidation tendency leads to the formation of a thin, insulating or semiconductive oxide layer that represents a capacity $C_{ox}$ connected in series with the Helmholtz capacity $C_H$, and leads to a gradual reduction in the total capacity, and hence to a corresponding increase in the respective required stimulation energy. In anodic polarity, OH$^-$ ions are drawn into the solid body, and there lead to an increase in the thickness of the oxide layer. The consequence of this is a further reduction in the phase limit capacity, and thus a further increase in the electrode impedance. The effect of the anodic pulses required for recognition of effectiveness in conventional charge integration methods is that the recognition of effectiveness cannot be performed with the known electrodes, or can only be performed with an increased quantity of energy.

Anodic polarity does not only occur in active counterpulses for recognition of effectiveness, however, but also in anodically polarized electrodes in multipolar pacemaker systems, or in impedance measurement in hearts. It can, moreover, be caused by overshootings of the stimulation pulses.

Hence, because of their relatively large surface area, conventionally coated, porous electrodes can initially achieve successful stimulation with low energy. It has been recognized that the Helmholtz capacity is reduced by the oxidation tendency, leading to an increase in the electrode impedance. The influence of the electrode properties caused by this over the duration of implantation is therefore very serious, because the deterioration in the electrode properties has effects that in turn contribute to the additional unfavorable influence on the stimulation properties. Thus, a higher energy is necessary in a deteriorating electrode, so recognition of effectiveness also requires a counterpulse with a higher pulse energy, which in turn contributes to the deterioration of the electrode properties. Because the pulse energy and the counterpulses required for recognition of effectiveness are set at values that must be valid for the entire duration of implantation of the pacemaker, in the end the worsening of the operational conditions essentially is based on measures that should actually counteract the worsened operating conditions.

The biocompatible surface coating of the stimulation electrode of the invention, which exhibits long-time stability, is composed of a material whose oxidation tendency is very low, and is preferably applied to the electrode using vacuum technology and a substantially inert material, such as a nitride, carbide, carbon nitride or a pure element or specific alloy from the group that includes gold, silver, platinum, iridium or carbon. Due to the fractal spatial geometry of a surface layer applied in this manner, its active surface area is very large, so the quantity of energy required for stimulation can be kept small.

The afterpotential of a stimulation electrode made of titanium and having a sputtered iridium layer produced by reactive cathodic sputtering is up to six times (from approx. 600 to approx. 100 mV) less than the afterpotential of a bare stimulation electrode made of titanium. Because of this significant reduction of the afterpotential, the recognition of the intracardiac EKG is not only possible in a conventional manner with an amplifier and a triggering apparatus, but an operative effectiveness recognition that requires no counterpulses can be used.

As a result of the reduction in required stimulation energy over the service life of the implant, otherwise necessary reserves can be omitted, and the operating time of the implant can be advantageously and decisively lengthened, or, as the case may be, the size of the housing can be reduced significantly.

A specific charge Q is required for successful stimulation. The necessary current also charges the Helmholtz capacity $C_H$; consequently, following stimulus, a voltage, the so-called afterpotential, can be measured via the condenser. Since the voltage falling at a condenser is inversely proportional to the capacity when the charge is constant, the afterpotential is also reduced by a high Helmholtz capacity $C_H$, which is achieved by the large active surface area of the stimulation electrode of the invention, and the temporal change in the afterpotential is reduced. Because the inert surface layer of the stimulation electrode of the invention has no or a very slight oxidation tendency, the electrode can be operated anodically—if nonetheless desired under certain conditions—without an oxide layer forming and/or its layer thickness d increasing, so the Helmholtz capacity $C_H$ can constantly be maintained at a high value, the afterpotential caused by the electrode can be kept as low as desired, and reliable effectiveness recognition thus assures optimization of the stimulation procedure.

The properties of the electrode of the invention are significantly improved with respect to prior electrodes by virtue of its fractal geometry, because the fractal-like, "cauliflower-like surface" creates porous structures that have a fine structure with a substantially increased surface area with respect to a surface that encloses the external geometry of the electrode. On the other hand, by means of the geometrical regions which, in connection with fractal geometry, have the rougher surface, areas are created that assure sufficient mechanical strength and serve as carriers for the regions having the finer geometric structure. It can therefore be seen that the active coating of the electrode has a geometric structure that becomes increasingly finer toward its surface. The size of the pores therefore decreases as they approach the surface. A structure of this type is comparable to a vascular system, which has in its peripheral regions a fine structure that opens into an increasingly coarse main vascular system.

Since the frequency spectrum of the intracardiac signals has a bandwidth of up to approximately 50 Hz, with a maximum of approximately 1 to 5 Hz, the transmission behavior, above all the considerable, low-frequency components of the frequency spectrum, can also be optimized if the Helmholtz capacity $C_H$ is maximized.

Another advantageous feature of the stimulation electrode of the invention is that the signal amplitudes are increased during detection, because the detected voltage in all frequency ranges of the overall impedance of the electrode system $Z_S$ and the phase limit impedance are based on the following equation (where $U_{EKG}$ corresponds to the voltage of the intracardiac EKG actually present in the heart):

$$U_{det} \approx U_{EKG} \left( \frac{Z_S - Z_{DL}}{Z_S} \right) \qquad (4)$$

and the impedance of the electrode system $Z_{DL}$ is minimized by the maximization of the Helmholtz capacity $C_H$.

Although the size of the active surface area could be changed by a simple enlargement of the electrode, it has been found that it is more advantageous to maximize the active surface area in relation to the surface area defined by the geometrical shape of the electrode, since a linear enlargement also only has as a consequence a surface area-proportional increase by approximation of the charge Q required for stimulation, and therefore does not represent a solution. This observation is clarified by the different influence range of the stimulation electrodes; more eloquently, a constant charge density would be required for heart muscle stimulation.

By virtue of their fractal geometry, the surface coatings of the invention, made of the above-named materials, and particularly of iridium nitride IrN, which are applied to conventional electrodes with the aid of modern vacuum-coating methods such as sputtering or ion-plating, assure a factor of 1000 and more in surface area enlargements. In fractal geometry, a number of an element is found repeated, but reduced, on larger elements having nearly the same shape. This assignment of shape can—at least approximately—be achieved with methods of thin-layer technology by setting the method parameters. The electrode of the invention also has surprisingly low stimulation threshold values over the long term.

With the option of utilizing anodic operation, the electrode can also be used advantageously in modes of operation in which this polarity is necessary for function, for example in bi- or multipolar electrodes or intracardiac impedance measurement.

The electrode of the invention is also suited in a preferable manner for neural stimulation, and generally for those types of stimulation purposes that are not dependent on high field strengths, but on low impedance and consequently large, local charge or current densities adjacent to the organ to be stimulated or the affected neural pathways, respectively.

BRIEF DESCRIPTION OF THE DRAWINGS

Advantages of the invention are disclosed in the dependent claims and described in detail below, together with the description of the preferred embodiment of the invention, by way of the drawing figures. Shown are in:

FIG. 1 a schematic representation of an embodiment of a stimulation electrode of the invention in side view, FIG. 2 an enlarged representation of detail II of FIG. 1 in section, FIG. 3 a diagram for comparing the impedance of the embodiment of the electrode in accordance with the invention with that of prior electrodes of corresponding, identical geometrical dimensions, FIG. 4 a representation of fractal surface geometry of the electrode in accordance with the invention, in which

DESCRIPTION OF THE PREFERRED EMBODIMENTS

Figure 1:
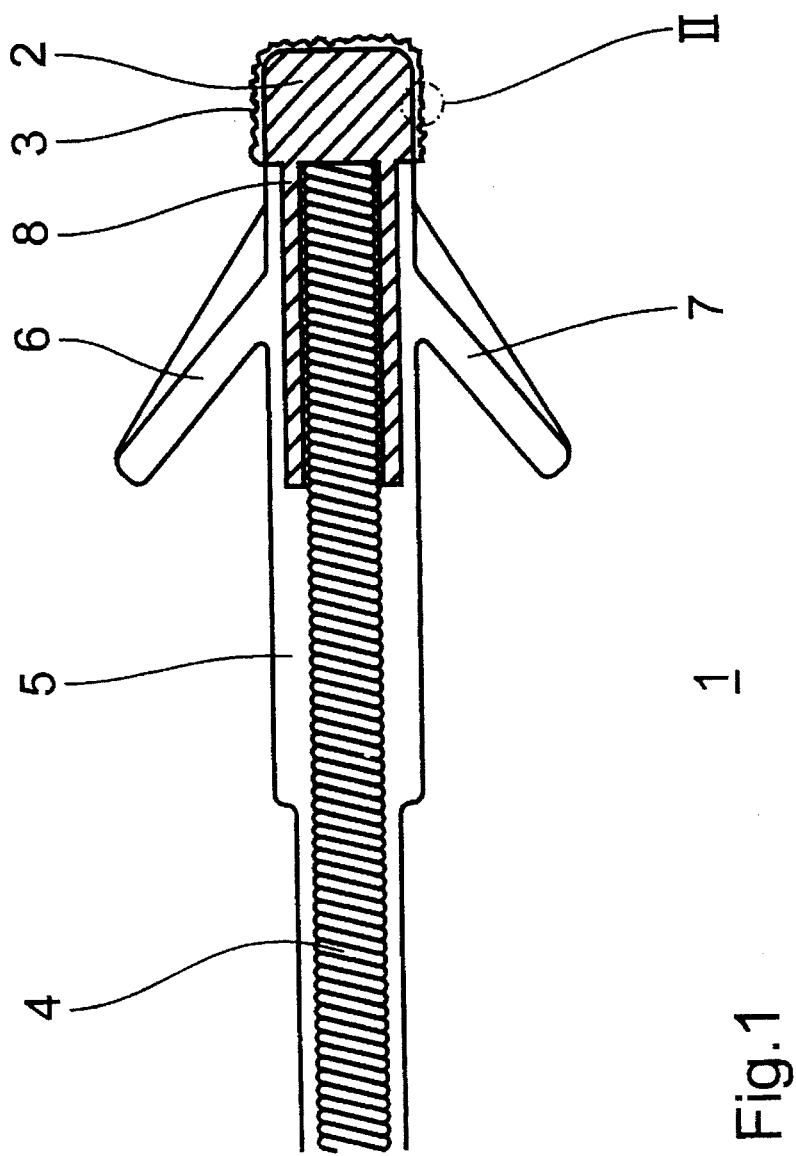

The stimulation electrode 1 shown in a schematic side view in FIG. 1 is a unipolar, burled electrode whose head has a cylindrical base body 2 of titanium. In accordance with the invention, the cylindrical base body 2 has a surface coating 3 composed of an inert material, iridium nitride (IrN), and is applied to the cylindrical base body 2 of the titanium electrode by means of cathode sputtering. The electrode has a coiled, electrically-conductive lead 4 that is provided with an electrically insulating casing 5 of silicon. In the drawing, this silicon casing is illustrated as being transparent. Integral to the silicon casing are two backward-oriented, flexible fastening elements 6 and 7, which serve to anchor the electrode in the heart by keeping the surface of the base body in contact with the inside surface of the heart.

The base body 2 is pushed over the lead 4 by means of a hollow, cylindrical joined-on piece 8 and secured there; this joined-on piece is shown in section in the drawing.

Figure 2:
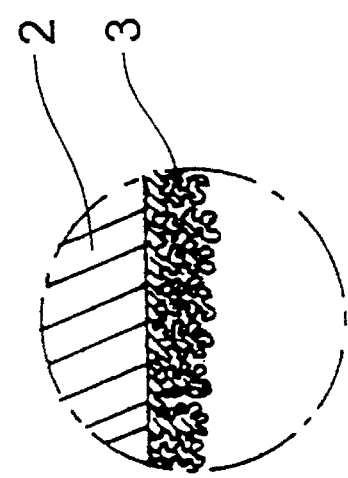

FIG. 2 shows a section (detail II in FIG. 1) of the active surface on an enlarged scale. As can be seen from the representation, a significant enlargement of the active surface area is attained by means of the fractal, spatial geometry (not enlarged to scale) of the coating 3, which has grown in the manner of a stem in the microscopic range. The achieved surface area enlargement is in a range of over 1000.

Figure 3:
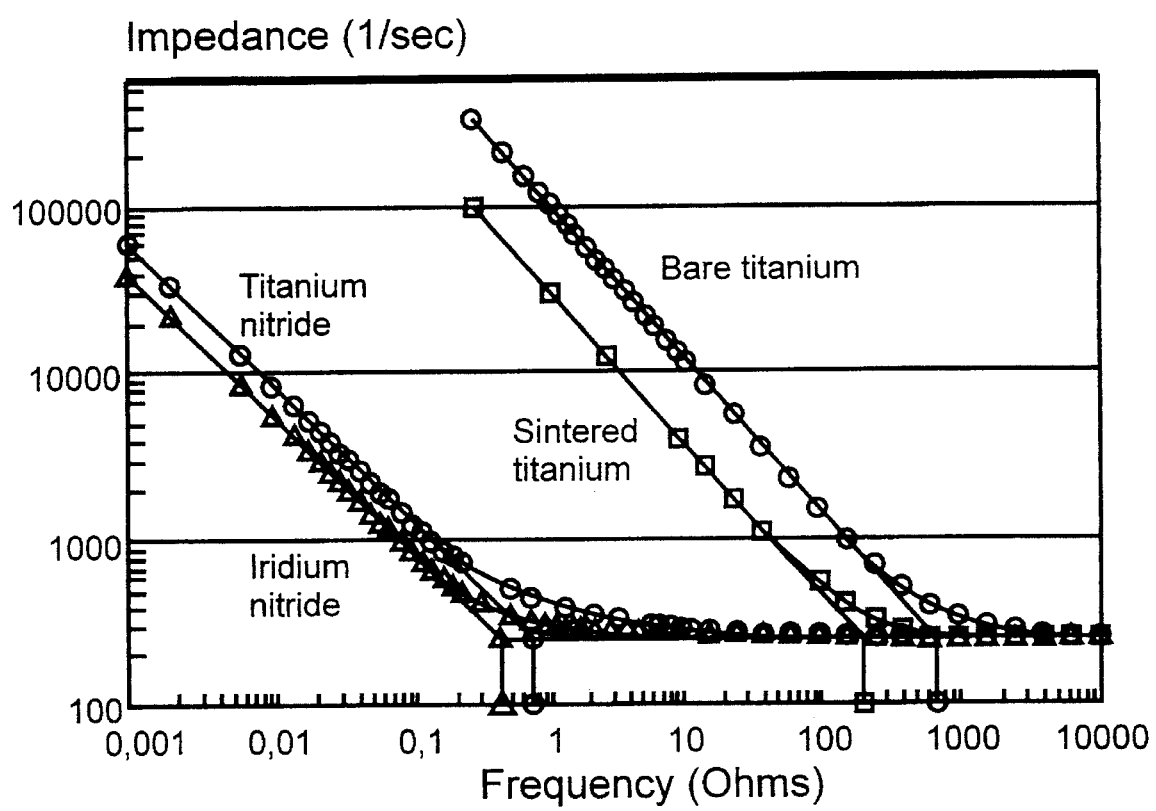

It can be seen from FIG. 3, which illustrates a comparison of the courses of the impedances of stimulation electrodes with different surface coatings, that an electrode coated with iridium nitride exhibits the lowest phase-limit impedance in comparison with the prior electrode surface coating materials titanium and titanium nitride, particularly smaller in range, in the low-frequency range that is particularly significant for receiving signals received from the heart. The determined differences are therefore of particular significance with regard to their effects, because the amplitude of the received signal is in a quadratic relationship with the inner resistance of the signal source.

Other embodiments of pacemaker electrodes in which anodic operation is desired are not shown in detail in the drawings. They are distinguished by a decreased surface area with respect to comparable, known electrodes, because certain surface reserves that had to be provided in the known electrodes for the case of impedance enlargement can be omitted. In bi- or multipolar electrodes, annular regions are provided that are removed from and opposite the electrode head and are provided with separate, galvanic connections to the connection-side end. By means of this, either a bipolar stimulation or an intracardiac impedance measurement for determining heart activity can be effected.

In the case that the pacemaker housing is used, a region of the housing oriented toward the body surface is provided with the coating of the invention, while the remaining part of the housing is provided with an insulating casing preferably composed of silicon caoutchouc.

Figure 4A:
FIG. 4a shows a coating with a basic geometrical shape.
Figure 4B:
FIG. 4b shows the basic geometrical shape scaled-down and superposed onto a larger basic geometrical shape.
Figure 4C:
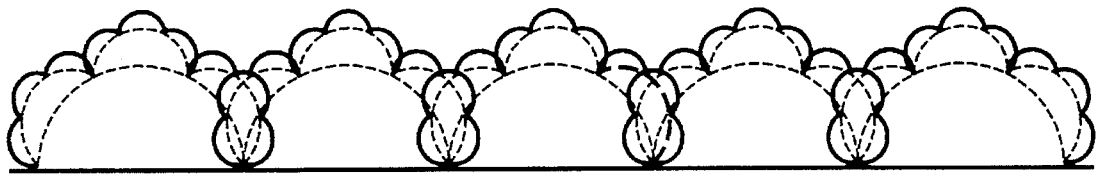
FIG. 4c shows the basic geometrical shape scaled-down and superposed onto a larger basic geometrical shape as in FIG. 4b and superposed onto a still larger basic geometrical shape, and FIG. 5 a section of the surface of the electrode in accordance with the invention in an enlarged representation.

It can be seen from the representation in FIGS. 4a through c how the basic shape of a semicircular cross-section is superposed in FIG. 4a by a Geometric shape that is correspondingly reduced to scale. The scaled-down shaping elements are added to the surface of the next larger basic shape. The next stage, that of superposition, is shown in FIG. 4c. The simplified illustration in these figures serves solely to represent the basic geometric relationships. In practical production, the basic forms can be superposed over spatially further stages.

Figure 5:

The electron-microscopically enlarged representation of FIG. 5 shows the surface of an electrode in accordance with the invention that exhibits a cauliflower-like exterior. The structure is irregularly shaped, but follows the outlined fractal laws. Because the structure becomes continuously finer toward the outside, a microscopic surface is attainable that is multiple times larger in terms of surface area than the associated macroscopic surface area.

The invention is not limited to the above-described, preferred embodiment. Rather, a number of variations is conceivable that makes use of the solution shown, even in fundamentally different types of embodiments.

What is claimed is:

1. A stimulation electrode, comprising:

an electrode base body which has a basic geometric shape and a surface area; and a porous surface coating which is provided on at least a portion of the electrode base body, which is comprised of an inert material having a low oxidation tendency effective to render the material substantially inert and being selected from the group consisting of a element, a chemical compound, and an alloy, which is porous and has a fractal spatial geometry, and which has an active surface area which is greater by a factor of at least one thousand times than the surface area of the electrode base body.

2. The stimulation electrode as defined in claim 1, wherein the inert material is selected from the group consisting of (a) an element selected from the group consisting of gold, iridium, platinum and carbon, (b) a chemical compound which is one of a nitride, a carbide or a carbon nitride of an element selected from the group consisting of gold, iridium, platinum and carbon, and (c) an alloy of at least two elements selected from the group consisting of gold, iridium, platinum and carbon.

3. The stimulation electrode as defined in claim 2, wherein the porous surface coating is composed of iridium nitride.

4. The stimulation electrode as defined in claim 1, wherein the electrode base body is composed of titanium.

5. The stimulation electrode as defined in claim 1, further comprising means for connecting the stimulation electrode to an anode terminal, and wherein the porous surface coating has an active surface area which is effective for anodic operation of the stimulation electrode.

6. A bipolar stimulation system, comprising:

a reference electrode which is a stimulation electrode according to claim 1; and means for connecting the reference electrode to a reference terminal.

7. A stimulation electrode, comprising:

an electrode base body which has a basic geometric shape and a surface area; and a porous surface coating which is a thin film applied to the electrode by a thin-layer technology process, which is provided on at least a portion of the electrode base body, which is comprised of an inert material having a low oxidation tendency effective to render the material substantially inert and being selected from the group consisting of a element, a chemical compound, and an alloy, which is porous and has a fractal spatial geometry, and which has an active surface area which is greater by a factor of at least one thousand times than the surface area of the electrode base body.

8. The stimulation electrode as defined in claim 7, wherein the thin film is a vacuum deposited thin film, and wherein the thin-layer technology process is a vacuum coating method selected from the group consisting of reactive cathodic sputtering and ion-plating.

* * * * *